United States Patent [19]

Bolton et al.

[11] 4,082,746

[45] Apr. 4, 1978

[54] 1,3-DIPHENYL-4 OR 5-SULPHOALKYL PYRAZOLINES

[75] Inventors: Ivan Joseph Bolton, Bingley; Alec Victor Mercer, Leeds, both of England

[73] Assignee: Sandoz Ltd., Basel, Switzerland

[21] Appl. No.: 725,853

[22] Filed: Sep. 23, 1976

Related U.S. Application Data

[62] Division of Ser. No. 601,279, Aug. 4, 1975, Pat. No. 3,997,556.

[30] Foreign Application Priority Data

| Aug. 9, 1974 | United Kingdom | 35129/74 |
| Feb. 10, 1975 | United Kingdom | 5523/75 |
| May 12, 1975 | United Kingdom | 1978/75 |

[51] Int. Cl.² .................................... C07D 231/06
[52] U.S. Cl. .................. 260/239.9; 548/379
[58] Field of Search ............... 260/239.9, 310 D

[56] References Cited

U.S. PATENT DOCUMENTS

| 3,836,522 | 9/1974 | Somlo et al. | 260/239.9 |
| 3,865,816 | 2/1975 | Mengler | 260/239.9 |
| 3,939,154 | 2/1976 | Bolton et al. | 260/239.9 |
| 3,997,556 | 12/1976 | Bolton et al. | 260/310 D |
| 4,003,889 | 1/1977 | Bolton et al. | 260/239.9 |

*Primary Examiner*—Natalie Trousof
*Assistant Examiner*—Jane T. Fan
*Attorney, Agent, or Firm*—Gerald D. Sharkin; Richard E. Vila; Thomas C. Doyle

[57] ABSTRACT

Disclosed are anionic optical brightening agents, such agents being 1,3-diphenyl pyrazolines characterized by having, in the 4- or 5-position of the pyrazoline ring, a sulphoalkyl substituent, their production and use.

11 Claims, No Drawings

1,3-DIPHENYL-4 OR 5-SULPHOALKYL PYRAZOLINES

This is a division of application Ser. No. 601,279 filed Aug. 4, 1975, now U.S. Pat. No. 3,997,556.

The invention relates to pyrazoline derivatives.

According to the invention there are provided anionic optical brightening agents, such agents being 1,3-diphenyl pyrazolines characterised by having, in the 4- or 5-position of the pyrazoline ring, a sulphoalkyl substituent.

The pyrazolines provided by the invention may be substituted, particularly in the phenyl nuclei thereof, by substituents not deleteriously affecting the brightening properties thereof, examples of suitable substituents being hereinafter given. The alkyl moiety of the sulphoalkyl substituent is preferably straight chain, of 1 to 3 carbon atoms, unsubstituted or substituted by methyl. The most preferred sulphoalkyl group is the sulphomethyl group, and the sulpho group may be in free acid or salt form. The sulphoalkyl group is preferably in the 4-position of the pyrazoline ring.

Representative of the compounds provided by the invention are the compounds of formula I,

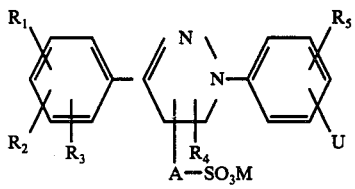

in which
$R_1$, $R_2$ and $R_3$, independently, signify hydrogen, chlorine, fluorine, $C_{1-4}$alkyl or $C_{1-4}$alkoxy,
$R_4$ signifies hydrogen, $C_{1-4}$alkyl or phenyl, preferably hydrogen,
A signifies a straight $C_{1-3}$alkylene chain, unsubstituted or substituted by methyl,
either
  $R_5$ signifies hydrogen, chlorine, $C_{1-4}$alkyl or $C_{1-4}$alkoxy, preferably hydrogen, and
  U signifies hydrogen, cyano, chlorine, $-SO_2R_6$, $-CO_2R_7$, $-SO_2NR_8R_9$ or $-CONR_8R_9$,
  in which $R_6$ signifies hydrogen or $C_{1-4}$alkyl, unsubstituted or mono-substituted by $-COOM$, $C_{1-4}$alkoxycarbonyl, aminocarbonyl or cyano,
  $R_7$ signifies hydrogen or $C_{1-4}$alkyl, unsubstituted or mono-substituted by $C_{1-4}$alkoxy, and
  $R_8$ and $R_9$, independently, signify hydrogen, phenyl, unsubstituted alkyl or alkyl mono-substituted by hydroxy,
or $R_5$ and U, together with the phenyl to which they are attached, signify a radical of formula (a),

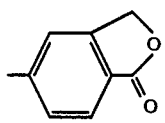

and M signifies a hydrogen atom or a non-chromophoric cation.

In the compounds of formula I, A preferably signifies an unsubstituted $C_{1-3}$alkylene chain, more preferably a methylene group. A is preferably bound at the 4-position of the pyrazoline ring. $R_1$, $R_2$ and $R_3$, independently, preferably signify hydrogen, chlorine or $C_{1-2}$alkyl, any alkyl more preferably being methyl. Moreover, at least one of $R_1$, $R_2$ and $R_3$ is preferably chlorine. Any alkyl or hydroxy-alkyl as $R_8$ or $R_9$ is preferably of 1 to 4 carbon atoms and where one of $R_8$ or $R_9$ is phenyl, the other is preferably other than phenyl. Where U and $R_5$ are not combined to form a lactone ring, U is preferably attached to the 4-position of the phenyl radical and its preferred significances are $-CN$, $-SO_2R_6'$, $-CO_2R_7'$, $-SO_2NR_8'R_9'$ and $-CONR_8'R_9'$, where $R_6'$ is $C_{1-4}$alkyl, mono-substituted by $-COOM$, $C_{1-4}$-alkoxycarbonyl, aminocarbonyl or $-CN$, or, preferably, unsubstituted, $R_7'$ is $C_{1-4}$alkyl, and $R_8'$ and $R_9'$, independently, are hydrogen or $C_{1-4}$alkyl. The more preferred significances of U, again where not combined with $R_5$, are $-CN$, $-SO_2NH_2$, $-SO_2R_6''$ and $-CO_2R_7''$, where $R_6''$ and $R_7''$ signify $C_{1-2}$alkyl. Compounds bearing the radical of formula (a) are also preferred. In the compounds of formula I, the $-A-SO_3M$ and $R_4$ groups are on different carbon atoms.

Thus, a preferred class of compounds of formula I is the class of formula I',

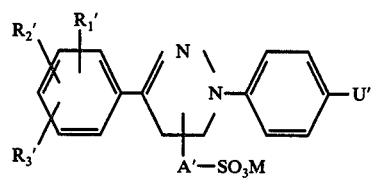

where
$R_1'$, $R_2'$ and $R_3'$, independently, signify hydrogen, chlorine or $C_{1-2}$alkyl, (preferably methyl), preferably at least one signifying chlorine,
A' signifies an unsubstituted straight $C_{1-3}$alkylene chain (preferably $-CH_2-$), preferably attached at the 4-position of the pyrazoline ring,
either
  U' signifies $-CN$, $-SO_2R_6'$, $-CO_2R_7'$ or $-SO_2NR_8'R_9'$,
  in which $R_6'$, $R_7'$, $R_8'$ and $R_9'$ are as defined above, or
  U' and the phenyl group to which it is attached signify a radical of formula (a), above, and
M is as defined above.

A preferred class of compounds of formula I' is the class of formula I'',

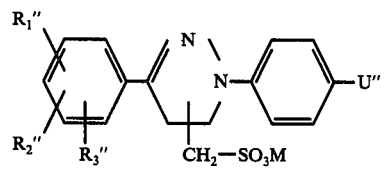

where the $-CH_2-SO_3M$ group is preferably attached to the 4-position of the pyrazoline ring,
$R_1''$, $R_2''$ and $R_3''$, independently, signify hydrogen, chlorine or methyl, preferably at least one signifying chlorine,
either U'' signifies $-CN$, $-SO_2NH_2$, $-SO_2R_6''$ or $-CO_2R_7''$, in which $R_6''$ and $R_7''$ are as defined above, or
U'' and the phenyl to which it is attached signify a radical of formula (a), above, and
M is as defined above.

In the compounds of formula I" one of $R_1''$, $R_2''$ and $R_3''$ preferably signifies a 4-chloro substituent, the other two either both being hydrogen or one a 2-methyl substituent, the other a 5-chloro substituent. The preferred significance of U" is either $-SO_2R_6''$, particularly $-SO_2CH_3$ or, together with the phenyl to which it is attached, a radical of formula (a). From the standpoint of ease of preparation, where the sulphomethyl group is in the 5-position, U" preferably signifies $-SO_2R_6''$ or $-CN$ or, together with the phenyl to which it is attached, a radical of formula (a), above.

In the compounds of formulae I, I' and I", the exact nature of M, when such is a cation, is not critical provided such cation is non-chromophoric. In general it may be any cation conventional in the optical brightener art, to which the present invention belongs. As examples of suitable cations may be given the alkali metal cations, such as of sodium or potassium, the alkaline-earth metal cations, such as of magnesium or calcium, and the substituted or unsubstituted ammonium cations, e.g., of formula $R_{10}R_{11}R_{12}NH^{\oplus}$, where $R_{10}$, $R_{11}$ and $R_{12}$, independently, signify hydrogen or $C_{1-4}$alkyl, unsubstituted or substituted by one or two, preferably one, hydroxy radical, for example the mono-, di- and tri-ethanolammonium and mono-, di- and tri-isopropanolammonium cations, as well as the simple ammonium cation. In any hydroxy-alkyl ammonium cation, the hydroxy group(s) is preferably at least two carbon atoms removed from the nitrogen. Any cation as M, however, is preferably sodium or potassium, particularly the former.

For the sake of simplicity, in the formulae herein given, M is shown to be mono-valent. It may, however, be di- or polyvalent. Where more than one M is present in the compounds, the M's may be the same or different.

The invention also provides a process for the production of the compounds of the present invention, which process comprises (a) reacting an alkali-metal sulphite or bisulphite with a 1,3-diphenylpyrazoline, substituted in the 4- or 5-position of the pyrazoline nucleus by an alkyl group bearing, as substituent, a leaving group or (b) obtaining a compound of the invention in which the sulphoalkyl group is in the 4-position of the pyrazoline nucleus by reacting an α-sulphoalkyl propiophenone, substituted in the β-position by a leaving group, with a phenyl hydrazine.

In particular, the invention provides a process for the production of compounds of formula I, characterized by
(ai) reacting a compound of formula II,

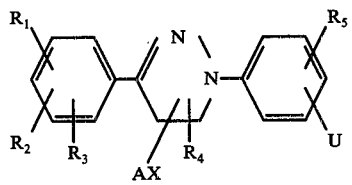

in which
$R_1$, $R_2$, $R_3$, $R_4$, $R_5$, A and U are as defined above, and
X signifies a leaving group,
with an alkali-metal suphite or bisulphite
(bi) obtaining a compound of formula Ia,

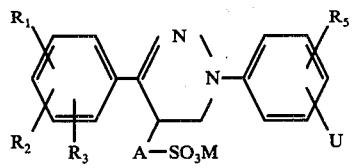

in which $R_1$, $R_2$, $R_3$, $R_5$, A, U and M are as defined above,
by reacting a compound of formula III,

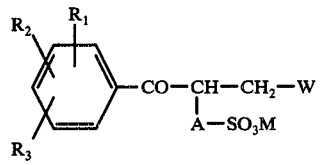

in which
$R_1$, $R_2$, $R_3$, A and M are as defined above, and
W signifies a leaving group, preferably amino, mono-($C_{1-4}$)-alkylamino, di-($C_{1-4}$)-alkylamino, morpholino, piperidino or pyrrolidino,
with a compound of formula IV,

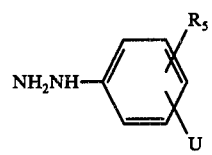

in which $R_5$ and U are as defined above, or (c) obtaining a compound of formula I in which $R_5$ and U, together with the phenyl to which they are attached, signify a radical of formula (a) by acid cyclisation of a compound of formula V,

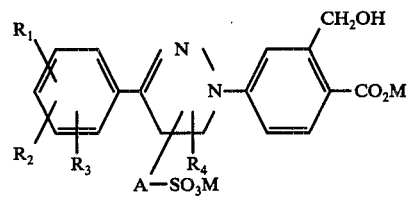

in which $R_1$ to $R_4$, A and M are as defined above.

The above processes may be carried out in manner conventional for the types of reaction involved.

Processes (a) and (ai) are suitably carried out by treatment of the starting material, e.g., the compound of formula II, with the alkali-metal sulphite or bisulphite in water or in a mixture of water and water-miscible solvent, e.g., ethanol, cellosolve or dioxan. The preferred alkali-metal sulphite or bisulphite is sodium sulphite or bisulphite. A suitable reaction temperature is from 20° to 150° C, preferably from 50° to 150° C. The preferred leaving groups, e.g., X in the compounds of formula II, are halogen and $-OSO_3H$. Where X is halogen, such is preferably chlorine and the reaction is most preferably carried out in a high boiling solvent, e.g., cellosolve, at reflux for from 24 to 48 hours.

Processes (b) and (bi) are suitably carried out in water, in a water-miscible solvent or in a mixture of water and a water-miscible solvent, examples of such solvents being ethanol, isopropanol, cellosolve, dioxan and dimethylformamide. A suitable reaction temperature is from 0° to 200° C, preferably from 20° to 150° C. The reaction is suitably carried out at a pH of from 1 to 11, preferably under neutral to slightly acid conditions, e.g., at a pH of from 3 to 7.

Process (c) is conveniently carried out in an aqueous or aqueous/inert water-miscible organic solvent medium. A suitable pH is from 1 to 6, preferably from 1 to 3. Mineral acids, e.g., hydrochloric acid or organic acids, e.g., formic acid, may be employed to create the acidic environment for cyclisation to take place. A suitable reaction temperature is from 20° to 150° C, preferably from 70° to 120° C.

Where, in any of the above processes (a), (ai), (b) and (bi), compounds are employed of the type where $R_5$, U and the phenyl to which they are attached, signify a radical (a), above, and alkaline conditions, sufficient to cause cleavage of the lactone ring, are employed, the ring may be reformed by treatment with acid according to the procedure of process (c), above.

Of the above processes, processes (b) and (bi) are preferred.

The resulting compounds of the invention may be isolated and purified in conventional manner.

The compounds of the type of formula II may be obtained in conventional manner from available starting materials. For example, those wherein X signifies —O—SO$_3$H may be obtained from corresponding compounds in which X signifies hydroxy by treatment with sulphuric acid at a temperature of from 0° to 50° C, preferably from 0° to 25° C. The compounds of the type of formula II, wherein X signifies halogen may be obtained again from the corresponding hydroxy compounds by first treating with p-toluenesulphonyl halide in an organic base, such as pyridine, or in an inert solvent containing such a base, at low temperatures, to form the corresponding tosylate, followed by refluxing in a high boiling non-aqueous solvent, such as cellosolve, for from 1 to 4 hours in the presence of a lithium halide, preferably lithium chloride.

Such corresponding compounds in which X signifies hydroxy, e.g., compounds of formula VII,

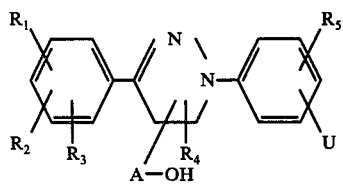

VII in which A, U and $R_1$ to $R_5$ are as defined above, form a further aspect of the present invention. They may be obtained by reacting a compound of formula VI,

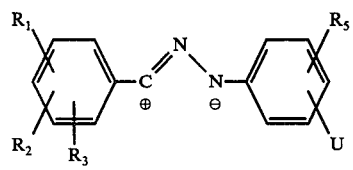

VI in which $R_1$ to $R_5$ and U are as defined above, with a compound of formula VIII,

VIII.

Such reaction is suitably carried out in conventional manner, for example in an inert organic solvent such as cellosolve or dioxan. A suitable reaction temperature is from 0° to 200° C, preferably from 20° to 150° C. This process generally yields mixtures of compounds of formula VII, i.e., a compound in which $R_4$ is in the 4-position of the pyrazoline ring and —A—OH in the 5-position, along with a compound in which $R_4$ is in the 5-position and —A—OH in the 4-position. Such mixtures may be separated in conventional manner where required, e.g., by chromatographic methods. Separation need not, however, be effected, the mixture being used as such for the production of compounds of formula II or for use as optical brightening agents as hereinafter described. Where, in the compounds of formula VIII, $R_4$ is hydrogen, the resulting compounds in which —A—OH is in the 5-position tend to predominate. The resulting compounds of formula VII may be isolated and purified in conventional manner.

In the compounds of formula VII, $R_1$ to $R_5$, U and A have the same preferred significances and positions as in in the compounds of formula I, I' and I", given above, save that A is preferably bound to the 5-position of the pyrazoline nucleus.

The compounds of formula V, employed in process (c) may be obtained in analogous manner to processes (ai) and (bi) but employing appropriate starting materials. Alternatively, they may be obtained by carrying out process (ai) or (bi) on compounds in which U and $R_5$, together with the phenyl to which they are attached, signify a radical of formula (a), above, under basic conditions such as to cleave the lactone ring.

The compounds of formulae III, IV, VI and VIII are known or may be obtained in conventional manner from available starting materials.

As will be appreciated, interconversion from one compound of formula I to another may be carried out in conventional manner. For example, compounds of formula I, in which U signifies —CN, may be converted into corresponding compounds, in which U signifies —COOH, in conventional manner, e.g., by treatment with hydrochloric acid in water or in a mixture of water and a water-miscible organic solvent, such as dioxan or acetic acid. A suitable temperature for such interconversion is from 20° to 150° C, preferably from 50° to 130° C. Further, compounds of formula I in which U is —COOH may be converted into the the corresponding esters in conventional manner employing appropriate esterification techniques.

Depending on the conditions used in the above processes and the significance of M in the starting materials, the desired significance of M can be introduced during the process. Alternatively, and as will be appreciated, the desired significance of M may be introduced subsequently in conventional manner, e.g., by conversion of salt forms of the resulting compounds to free acid forms or vice versa and by salt interconversions.

The anionic optical brightening agents of the invention, particularly the compounds of formula I, are useful as optical brightening agents for natural and synthetic polyamide fibres, particularly for Nylon 6 and Nylon 6.6 fibres. Thus, the invention also provides a process for optically brightening a fibrous substrate comprising natural or synthetic polyamide fibres, preferably Nylon 6 or Nylon 6.6 fibres, comprising applying thereto, as brightening agent, an anionic brightening agent according to the invention.

The anionic brighteners may be applied to the substrate, which may be, for example, in yarn, non-woven, woven, knitted or other form, in conventional manner using conventional amounts, the brighteners being particularly indicated for application by the so-called "Thermosol" application method, (Gunn & Nightingale "Cotton and Man-Made Fibres Year Book" 1966-7 p. 410). In such process, the compounds are applied in amounts of from 0.01 to 0.7%, preferably 0.05 to 0.3%, based on the weight of the substrate. The substrate is padded with liquor containing the compound at a temperature of from 0° to 60° C, preferably 10° to 50° C, at a pick-up of from 20 to 120%, preferably 40 to 90%, the liquor containing such additives as surfactants and pH adjusting agents, e.g., formic acid, as desired. The subsequent heat treatment is applied for 5 to 120 secs, preferably 15 to 60 secs, the temperature being 140° to 190° C, preferably 160° to 185° C, for Nylon 6, and 140° to 220° C, preferably 170° to 200° C, for Nylon 6.6. They may also be applied using acid flash and acid exhaust techniques.

The compounds of formula VII are likewise optical brightening agents and are suitable for the brightening of natural and synthetic polyamide substrates employing the same general methods as for compounds of formula I type. They are, however, applied as aqueous dispersions rather than as solutions and tend, in general, to give somewhat inferior results to those obtained using compounds of the type of formula I.

The compounds of formula VII also give brightening effects when applied to polyacrilonitrile substrates in conventional manner, for example by exhaustion from aqueous acidified dispersions. Suitable amounts of brightener lie in the range of from 0.001 to 0.05%, preferably from 0.01 to 0.2% by weight based on the weight of the substrate.

The following Examples, in which all parts and percentages are by weight, unless otherwise stated, and all temperatures are in degrees centigrade, illustrate the invention.

EXAMPLE 1 (PROCESS (b))

34.75g of 3-(4"-morpholino)-2-sulphomethylene-(4'-chloropropiophenone) internal salt, 20.5g of p-methyl-sulphonyl phenyl hydrazine, and 40.5g of anhydrous sodium acetate were slurried in a mixture of 100 ml water and 100 ml cellosolve. The mixture was heated to the boil and stirred under reflux for 16 hours. The resultant solution was evaporated to dryness and the residue was extracted with 500 ml hot cellosolve. The cellosolve extract was evaporated to dryness and the residue was slurried with 250 ml hot ethanol, then cooled and filtered to give the pyrazoline

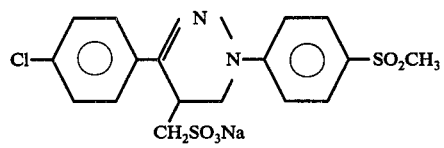

as a pale yellow solid.

The 3-(4"-morpholino)-2-sulphomethylene-(4'-chloropropiophenone) internal salt was obtained as follows:

28.22g of 3,4'-dichloropropiophenone, slurried in 56 ml ethanol, was treated with a solution of 30.65g of anhydrous sodium sulphite in 168 ml water. The mixture was heated to the boil, stirred under reflux for 5 hours, then cooled to 0°-5° and filtered. The filter cake was washed with four 28 ml portions of 10% brine and the resultant solid was dried. The white solid thus obtained was slurried in 125 ml cellosolve with 17.0g of morpholine hydrochloride and 4.13g of paraformaldehyde. The mixture was heated to the boil, stirred under reflux for 1 hour, cooled to 0°-5° and filtered. The filter cake was washed with three 25 ml portions of ice cold ethanol and dried to give a white solid containing 34.75g of 3-(4"-morpholino)-2-sulphomethylene-(4'-chloropropiophenone) internal salt.

Following the procedure of Example 1, above, and using appropriate starting materials, the compounds in the following table are obtained.

| Example | Compound | Appearance |
|---|---|---|
| 2 | Cl—⟨○⟩—C(=N-N(—⟨○⟩—SO₂NH₂)—CH₂—)—CH₂SO₃Na | pale yellow solid |
| 3 | Cl—⟨○⟩(CH₃)(Cl)—C(=N-N(—⟨○⟩—SO₂CH₃)—CH₂—)—CH₂SO₃Na | pale yellow solid |
| 4 | Cl—⟨○⟩(CH₃)(Cl)—C(=N-N(—⟨○⟩—SO₂NH₂)—CH₂—)—CH₂SO₃Na | pale yellow solid |

-continued

| Example | Compound | Appearance |
|---|---|---|
| 5 | 2,4-Cl,Cl-5-CH3-C6H2-C(=N-N(CH2SO3Na)-)-CH2-N(C6H4-SO2NH2) (structure with CH3, Cl, Cl on phenyl; C=N-N; CH2SO3Na; linked to C6H4-SO2NH2) | pale yellow solid |
| 6 | 2,5-(CH3)2-4-Cl-C6H2-C(=N-N-)-CH(CH2SO3Na)-CH2-N-C6H4-SO2NH2 | pale yellow solid |
| 6a | 2-CH3-4,5-Cl2-C6H2-C(=N-N-)-CH(CH2SO3Na)-CH2-N-C6H4-CO2CH3 | pale yellow solid |
| 6b | 4-Cl-C6H4-C(=N-N-)-CH(CH2SO3Na)-CH2-N-C6H4-CO2CH2CH2OCH2CH3 | pale yellow solid |
| 6c | 4-Cl-C6H4-C(=N-N-)-CH(CH2SO3Na)-CH2-N-C6H4-SO2CH2CH3 | pale yellow solid |
| 6d | 4-F-C6H4-C(=N-N-)-CH(CH2SO3Na)-CH2-N-C6H4-CO2NH2 | pale yellow solid |
| 6e | 4-CH3O-C6H4-C(=N-N-)-CH(CH2SO3Na)-CH2-N-C6H4-CO2NHCH2CH3 | pale yellow solid |
| 6f | 4-Cl-C6H4-C(=N-N-)-CH(CH2SO3Na)-CH2-N-C6H4-CO2N(CH3)2 | pale yellow solid |
| 6g | C6H5-C(=N-N-)-CH(CH2SO3Na)-CH2-N-C6H4-SO2NHCH2CH3 | pale yellow solid |
| 6h | 4-Cl-C6H4-C(=N-N-)-CH(CH2SO3Na)-CH2-N-(3-Cl-4-(SO2NH-C6H5)-C6H3) | pale yellow solid |

| Example | Compound | Appearance |
|---|---|---|
| 6i | Cl—⟨C₆H₄⟩—C(=N−N(CH₂—)−⟨C₆H₄⟩—SO₂N(CH₂CH₂OH)₂)−CH(CH₂SO₃Na) | pale yellow solid |

EXAMPLE 7 (PROCESS (a))

36.45g of 1-(p-methylsulphonylphenyl)-3-(p-chlorophenyl)-5-hydroxymethylene-Δ²-pyrazoline was slurried in 200 ml of dry pyridine and cooled to 0°. 21.0g of p-toluene sulphonyl chloride was added, and the mixture was allowed to warm to ambient temperature and stirred for 16 hours. The mixture was poured onto 400 ml of water and 400 g of ice and the resultant solid was filtered and washed with 200 ml of water. The wet cake was pulled as dry as possible, and the crude product was slurried in 200 ml of cellosolve. 8.5 g of lithium chloride was added, the mixture was heated to the boil and stirred under reflux for one hour. 200 ml of water was added, the mixture was cooled, filtered and washed with 200 ml of water. The wet crude solid was slurried with 63.0 g of anhydrous sodium sulphite in 400 ml of cellosolve and 400 ml of water. The mixture was heated to the boil, stirred under reflux for 16 hours, and then evaporated to dryness. The residue was extracted with 1 liter of boiling cellosolve, the cellosolve extract evaporated to dryness, and the resultant solid slurried with 200 ml of ethanol, cooled and filtered to give the pyrazoline

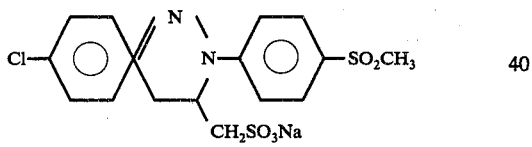

as a white solid.

The 1-(p-methylsulphonylphenyl)-3-(p-chlorophenyl)-5-hydroxymethylene-Δ²-pyrazoline was obtained as follows:

26.25 g of p-chlorobenzoyl chloride was added over 5 minutes to a well stirred suspension of 29.3 g of p-methyl sulphonyl phenyl hydrazine in 150 ml of dry pyridine at 0°–5°. The mixture was allowed to warm to ambient temperature and stirred for 16 hours. The mixture was poured onto 450 ml of water and 450 g of ice, and the resultant solid was filtered, washed with 450 ml of water and dried. The dried solid was slurried with 40.6 g of phosphorous pentachloride in 150 ml of dry diethyl ether. The mixture was heated to the boil, stirred under reflux for 16 hours, and then cooled to 5°. A solution of 64.5 g of phenol in 150 ml of ether was added over 15 minutes, followed by 90 ml of methanol over 5 minutes. The mixture was stirred for a further 15 minutes and was then evaporated to half volume. The remaining mixture was cooled to −10° to −20° for 16 hours, then filtered, washed with 150 ml 50% ethanol/water, and dried. The dried solid was slurried in 74.8 ml of allyl alcohol and 44.4 ml of triethylamine was added dropwise over 5 minutes. The resultant mixture was heated to the boil, stirred under reflux for 16 hours, and evaporated to dryness. The residue was slurried with 220 ml of ethanol and 220 ml of water, heated to the boil, then cooled and filtered to give 36.45 g of 1-(p-methylsulphonyl phenyl)-3-(p-chlorophenyl)-5-hydroxymethylene-Δ²-pyrazoline of formula,

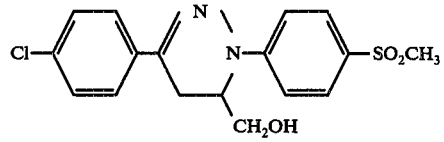

Following the procedure of Example 7, above, and using appropriate starting materials, the compounds in the following table are obtained.

| Example | Compound | Appearance |
|---|---|---|
| 8 | Cl—⟨C₆H₄⟩—C(=N−N−⟨C₆H₄⟩—CN)−CH(CH₂SO₃Na) | pale yellow solid |
| 9 | Cl—⟨C₆H₃(CH₃)(Cl)⟩—C(=N−N−⟨C₆H₄⟩—SO₂CH₃)−CH(CH₂SO₂CH₃) | white solid |

-continued

| Example | Compound | Appearance |
|---|---|---|
| 10 | [structure: 4,5-dichloro-2-methylphenyl with C=N-N linkage to 4-cyanophenyl, and CH₂SO₃Na branch] | pale yellow solid |
| 11 | [structure: 4,5-dichloro-2-methylphenyl with C=N-N linkage to 4-SO₂CH₃-phenyl, and CH₂SO₃Na branch] | pale yellow solid |
| 11a | [structure: 4-chlorophenyl with C=N-N linkage to 4-SO₂CH₃-phenyl, and CH₂CH₂SO₃Na branch] | pale yellow solid |
| 11b | [structure: 4-chlorophenyl with C=N-N linkage to 4-SO₂CH₃-phenyl, with CH₃ and CH₂SO₃Na branches] | pale yellow solid |
| 11c | [structure: 4-chlorophenyl with C=N-N linkage to phthalide, and CH₂SO₃Na branch] | pale yellow solid |
| 11d | [structure: 4,5-dichloro-2-methylphenyl with C=N-N linkage to phthalide, and CH₂SO₃Na branch] | pale yellow solid |

The compounds are obtained from the corresponding compounds of formula VII, i.e., compounds identical to those in the above table save for having the grouping —CH₂OH or —CH₂CH₂OH in place of the grouping —CH₂SO₃Na or —CH₂CH₂SO₃Na, respectively.

EXAMPLE 12 (PROCESS (b))

39.6 g of 3-(4''-morpholino)-2-sulphomethylene-(3', 4'-dichloro-6'-methylpropiophenone) internal salt, 21.0 g of 5-hydrazinophthalide hydrochloride, and 24.6 g of anhydrous sodium acetate were slurried in a mixture of 200 ml of water and 100 ml of cellosolve. The mixture was heated to the boil and stirred under reflux for 4 hours. 10 g of sodium chloride was added to the hot reaction mixture, which was then cooled and filtered to give the pyrazoline

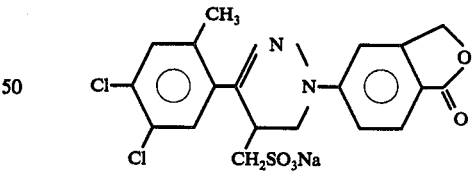

as a pale yellow solid.

The 3-(4''-morpholino)-2-sulphomethylene-(3',4'-dichloro-6'-methylpropiophenone) internal salt was obtained as follows:

50.3 g of 3,3',4'-trichloro-6'-methylpropiophenone was slurried in 100 ml of ethanol, and a solution of 28.0 g of anhydrous sodium sulphite in 300 ml of water was added. The resultant mixture was heated to the boil and stirred under reflux for 4 hours. The mixture was then cooled, filtered, washed with two 100 ml portions of cold water, and dried. The resultant white solid was slurried in 150 ml of cellosolve with a mixture of 34.8 g of morpholine, 43.1 g of sulphuric acid (d 1.84), and 12.0 g of paraformaldehyde. The mixture was heated to the boil and stirred under reflux for 2 hours. The mixture was then cooled, filtered, washed with 50 ml of cold water and three 100 ml portions of hot water (60°–70° C), and dried to give 39.6 g of 3-(4''-morpholino)-2-sulphomethylene-(3',4'-dichloro-6'-methylpropiophenone) internal salt as a white solid.

EXAMPLE 13

By following the procedure of Example 12 but using appropriate starting materials the pyrazoline

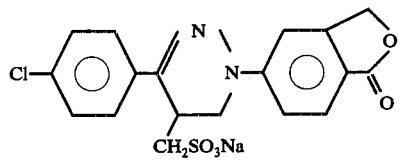

is obtained as a pale yellow solid.

APPLICATION EXAMPLE A

A strip of white Nylon 6.6, 15 cm wide and weighing 8 gms, was padded at 100% expression through a solution containing 0.2% of the pyrazoline produced in Example 1, 2% of a non-ionic alkylene oxide adduct of an alkylated phenol, and 0.2% formic acid. The nylon piece was dried at 80° and then passed through an oven at 180° for 30 seconds. The treated piece showed a brilliant whiteness compared with the untreated piece.

Similar results were obtained using the compounds of Examples 3 and 12.

APPLICATION EXAMPLE B

A 5 gm piece of white nylon 6.6 was treated with 200 mls of a solution containing 25 milligrams of the pyrazoline produced in Example 11 and 150 mg of acetic acid. The piece was entered at 40°, the temperature of the bath increased to 90°–100° over 30 minutes and then maintained at 90°–100° for a further 30 minutes. The piece was removed from the bath, rinsed in cold demineralised water and dried in an oven at 80°. The treated piece showed a brilliant whiteness compared to the untreated piece.

Similar results were obtained employing the compound of Example 12 and 13.

Brightening effects were also obtained when 1-(p-methyl-sulphonyl phenyl)-3-(p-chlorophenyl)-5-hydroxymethylene-$\Delta^2$-pyrazoline, (described as an intermediate in the preparation of the compound of Example 7) was applied in like manner. The 5-hydroxymethylene pyrazoline was introduced as a 10% dispersion in water containing a carboxylated ethylene oxide adduct of a fatty alcohol.

APPLICATION EXAMPLE C

A strip of nylon 6.6, 15 cms wide and weighing 8 gm was padded at 100% expression through a solution containing 0.2% of the pyrazoline produced in Example 1. The nylon piece was boiled for 1 minute in 240 ml of water containing 0.2% acetic acid, and was then washed off in boiling water for 1 minute. The piece was then rinsed in cold demineralised water and dried in an oven at 80°. The treated piece showed a brilliant whiteness compared to the untreated piece.

Similar results were obtained using the compound of Example 12 and 13.

APPLICATION EXAMPLE D

A 5 gm piece of white polyacrylonitrile was entered at room temperature into 200 ml of a mixture of 15 mg of 1-(p-methylsulphonyl phenyl)-3-(p-chlorophenyl)-5-hydroxymethylene-$\Delta^2$-pyrazoline (introduced as a 10% dispersion in water containing a carboxylated ethylene oxide adduct of a fatty alcohol), 15 mg of acetic acid and water. The temperature of the liquor was raised to 90° C over 30 minutes, and maintained at 90°–100° C for a further 60 minutes. The piece was then removed from the dyebath, rinsed in hot, then cold, demineralized water, and dried in an oven at 80° C. The treatment imparted a brilliant whiteness to the fabric.

What is claimed is:

1. A compound, of formula I,

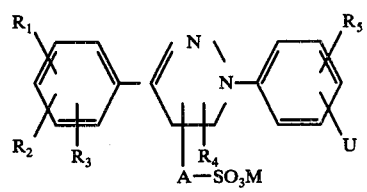

in which
$R_1$, $R_2$ and $R_3$, independently, signify hydrogen, chlorine, fluorine, $C_{1-4}$alkyl or $C_{1-4}$alkoxy,
$R_4$ signifies hydrogen, $C_{1-4}$alkyl or phenyl,
A signifies a straight $C_{1-3}$alkylene chain, unsubstituted or substituted by methyl,
$R_5$ signifies hydrogen, chlorine, $C_{1-4}$alkyl or $C_{1-4}$alkoxy, and
U signifies hydrogen, cyano, chlorine, —$SO_2R_6$, —$CO_2R_7$, —$SO_2NR_8R_9$ or —$CONR_8R_9$, in which $R_6$ signifies hydrogen or $C_{1-4}$alkyl, unsubstituted or mono-substituted by —COOM, $C_{1-4}$alkoxycarbonyl, aminocarbonyl or cyano,
$R_7$ signifies hydrogen or $C_{1-4}$alkyl, unsubstituted or mono-substituted by $C_{1-4}$alkoxy, and
$R_8$ and $R_9$, independently, signify hydrogen, phenyl, unsubstituted alkyl or alkyl mono-substituted by hydroxy, and
M signifies a hydrogen atom or a non-chromophoric cation selected from the group consisting of alkali metal cations, alkaline-earth metal cations and ammonium cations of the formula $R_{10}R_{11}R_{12}NH^{\oplus}$ where $R_{10}$, $R_{11}$ and $R_{12}$, independently signify hydrogen or $C_{1-4}$alkyl unsubstituted or substituted by one or two hydroxy radicals.

2. A compound of claim 1, wherein U is cyano.
3. A compound of claim 1, wherein U is —$SO_2R_6$.
4. A compound of claim 1, wherein U is —$CO_2R_7$.
5. A compound of claim 1, wherein U is —$SO_2NR_8R_9$.
6. A compound of claim 1, wherein U is —$CONR_8R_9$.
7. A compound of claim 1, of formula I',

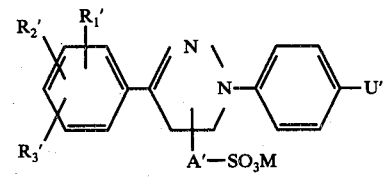

where $R_1'$, $R_2'$ and $R_3'$, independently, signify hydrogen, chlorine or $C_{1-2}$alkyl, A' signifies an unsubstituted straight $C_{1-3}$-alkylene chain, and U' signifies —CN, —$SO_2R_6'$, —$CO_2R_7'$, —$CONR_8'R_9'$ or —$SO_2NR_8'R_9'$, in which $R_6'$ is $C_{1-4}$alkyl, unsubstituted or mono-substituted by —COOM, $C_{1-4}$alkoxycarbonyl, aminocarbonyl or —CN, $R_7'$ is $C_{1-4}$alkyl and $R_8'$ and $R_9'$, independently, are hydrogen or $C_{1-4}$alkyl.

8. A compound of claim 7, wherein U' signifies —CN, —$SO_2R_6'$, —$CO_2R_7'$ or —$SO_2NR_8'R_9'$.

9. A compound of claim 7, of formula I'',

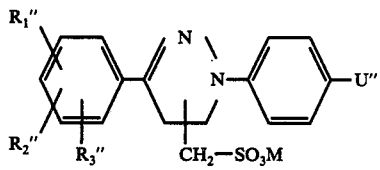

$R_1''$, $R_2''$ and $R_3''$, independently, signify hydrogen, chlorine or methyl, U'' signifies —CN, —$SO_2NH_2$, —$SO_2R_6''$ or —$CO_2R_7''$, in which $R_6''$ and $R_7''$ are $C_{1-2}$alkyl.

10. A compound of claim 9, wherein one of $R_1''$, $R_2''$ and $R_3''$ signifies a 4-chloro substituent.

11. A compound of claim 9, wherein U'' is other than —$COOR_7''$.

* * * * *